(12) United States Patent
Zhang et al.

(10) Patent No.: US 9,217,180 B2
(45) Date of Patent: Dec. 22, 2015

(54) OLIGONUCLEOTIDE PRIMER WITH OMEGA STRUCTURE FOR DETECTING SHORT-CHAIN RNAS AND USE THEREOF

(71) Applicant: Chengdu Nuoen Biological Technology Co., LTD, Chengdu (CN)

(72) Inventors: Songbo Zhang, Chengdu (CN); Guobiao Jiang, Chengdu (CN); Fang Tang, Chengdu (CN); Feifei Zhang, Chengdu (CN)

(73) Assignee: Chengdu Nuoen Biological Technology Co., Ltd., Chengdu, Sichuan Province (CN)

( * ) Notice: Subject to any disclaimer, the term of this patent is extended or adjusted under 35 U.S.C. 154(b) by 0 days.

(21) Appl. No.: 14/373,305

(22) PCT Filed: Jan. 16, 2013

(86) PCT No.: PCT/CN2013/070525
§ 371 (c)(1),
(2) Date: Jul. 18, 2014

(87) PCT Pub. No.: WO2013/107344
PCT Pub. Date: Jul. 25, 2013

(65) Prior Publication Data
US 2015/0056623 A1    Feb. 26, 2015

(30) Foreign Application Priority Data

Jan. 19, 2012  (CN) .......................... 2012 1 0016587
Apr. 13, 2012  (CN) .......................... 2012 1 0108312

(51) Int. Cl.
C12Q 1/68    (2006.01)

(52) U.S. Cl.
CPC ............ *C12Q 1/6876* (2013.01); *C12Q 1/6816* (2013.01)

(58) Field of Classification Search
None
See application file for complete search history.

(56) References Cited

U.S. PATENT DOCUMENTS

| 6,692,915 B1 * | 2/2004 | Nallur ................. C12Q 1/6874 435/173.1 |
| 2012/0045768 A1 * | 2/2012 | Arunachalam ...... C12Q 1/6813 435/6.12 |
| 2012/0164651 A1 * | 6/2012 | Kazakov ............... C12Q 1/682 435/6.12 |

FOREIGN PATENT DOCUMENTS

CN    101082060 A    12/2007

OTHER PUBLICATIONS

Lao et al. (Multiplexing RT-PCR for the detection of multiple miRNA species in small samples, Biochem Biophys Res Commun. Apr. 28, 2006;343(1):85-9. Epub Feb. 28, 2006).*
Chen et al. (Real-time quantification of microRNAs by stem-loop RT-PCR, Nucleic Acids Res. Nov. 27, 2005;33(20):e179).*
Kramer et al. (Stem-Loop RT-qPCR for miRNAs, Curr Protoc Mol Biol. Jul. 2011;Chapter 15:Unit 15.10).*
Schmittgen et al. (Real-time PCR quantification of precursor and mature microRNA, Methods. Jan. 2008;44(1):31-8).*
Raymond et al. (Simple, quantitative primer-extension PCR assay for direct monitoring of microRNAs and short-interfering RNAs, RNA. Nov. 2005;11(11):1737-44).*
Zeng et al (Structural requirements for pre-microRNA binding and nuclear export by Exportin 5, Nucleic Acids Res. Sep. 8, 2004;32(16):4776-85. Print 2004).*
Starega-Roslan et al. (Structural basis of microRNA length variety, Nucl. Acids Res. (2010), doi: 10.1093/nar/gkq727, First published online: Aug. 25, 2010).*
Caifu Chen et al. Real-time quantification of microRNAs by stem-loop RT-PCR. Nucleic Acids Research. Nov. 27, 2005, vol. 33, No. 20, pp. 1-9.
Chen, Xin et al. miRNA Quantification Methods Basing on PCR Technique. China Biotechnology 2010, vol. 30, No. 11, 99. 88-93.

* cited by examiner

*Primary Examiner* — Stephanie K Mummert
*Assistant Examiner* — Aaron Priest
(74) *Attorney, Agent, or Firm* — Novoclaims Patent Services LLC; Mei Lin Wong

(57) ABSTRACT

Disclosed are an oligonucleotide primer with an omega structure for detecting short-chain RNAs and the use thereof. The primer from the 5' end to the 3' end sequentially is: a PCR primer target region of 20-30 bases, a variable coding region of 0-50 bases, an omega stem-loop, a probe spacer of at least one base and a probe region of 4-11 bases. The length of the stem of the omega stem-loop is 4-12 paired bases, and the length of the loop of the omega stem-loop is 3-20 unpaired bases.

25 Claims, 5 Drawing Sheets

SEQUENCE LISTING

```
<160> NUMBER OF SEQ ID NOS: 26

<210> SEQ ID NO 1
<211> LENGTH: 50
<212> TYPE: DNA
<213> ORGANISM: Artificial Sequence
<220> FEATURE:
<223> OTHER INFORMATION: The sequence is synthesized.

<400> SEQUENCE: 1
gtgctgagtc acgaggtatt ctaggctctt tttagagcca tcctgtcagt          50

<210> SEQ ID NO 2
<211> LENGTH: 60
<212> TYPE: DNA
<213> ORGANISM: Artificial Sequence
<220> FEATURE:
<223> OTHER INFORMATION: The sequence is synthesized.

<400> SEQUENCE: 2
ggacctacta ctattcgtta ttgactgact tgtacttcca gaattaatcg agattgactg   60

<210> SEQ ID NO 3
<211> LENGTH: 42
<212> TYPE: DNA
<213> ORGANISM: Artificial Sequence
<220> FEATURE:
<223> OTHER INFORMATION: The sequence is synthesized.

<400> SEQUENCE: 3
gtgctgagtc acgaggtatt ctacgtgact cagcacgtca gt                  42

<210> SEQ ID NO 4
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 4
gtgctgagtc acgaggtatt ctagtcagt                                29

<210> SEQ ID NO 5
<211> LENGTH: 49
<212> TYPE: DNA
<213> ORGANISM: Artificial Sequence
<220> FEATURE:
<223> OTHER INFORMATION: The sequence is synthesized.

<400> SEQUENCE: 5
gtgctgagtc acgaggtatt ctaggcactc tttttagagt gccgtcagt           49
```

<210> SEQ ID NO 6
<211> LENGTH: 50
<212> TYPE: DNA
<213> ORGANISM: Artificial Sequence
<220> FEATURE:
<223> OTHER INFORMATION: The sequence is synthesized.

<400> SEQUENCE: 6
gtgctgagtc acgaggtatt ctaggcactc tttttagagt gccagtcagt       50

<210> SEQ ID NO 7
<211> LENGTH: 51
<212> TYPE: DNA
<213> ORGANISM: Artificial Sequence
<220> FEATURE:
<223> OTHER INFORMATION: NONE

<400> SEQUENCE: 7
gtgctgagtc acgaggtatt ctaggcactc tttttagagt gccatgtcag t      51

<210> SEQ ID NO 8
<211> LENGTH: 52
<212> TYPE: DNA
<213> ORGANISM: Artificial Sequence
<220> FEATURE:
<223> OTHER INFORMATION: The sequence is synthesized.

<400> SEQUENCE: 8
gtgctgagtc acgaggtatt ctaggcactc tttttagagt gccatcgtca gt     52

<210> SEQ ID NO 9
<211> LENGTH: 53
<212> TYPE: DNA
<213> ORGANISM: Artificial Sequence
<220> FEATURE:
<223> OTHER INFORMATION: The sequence is synthesized.

<400> SEQUENCE: 9
gtgctgagtc acgaggtatt ctaggcactc tttttagagt gccattcgtc agt    53

<210> SEQ ID NO 10
<211> LENGTH: 54
<212> TYPE: DNA
<213> ORGANISM: Artificial Sequence
<220> FEATURE:
<223> OTHER INFORMATION: The sequence is synthesized.

<400> SEQUENCE: 10
gtgctgagtc acgaggtatt ctaggcactc tttttagagt gccattccgt cagt   54

<210> SEQ ID NO 11
<211> LENGTH: 55
<212> TYPE: DNA
<213> ORGANISM: Artificial Sequence
<220> FEATURE:
<223> OTHER INFORMATION: The sequence is synthesized.

<400> SEQUENCE: 11
gtgctgagtc acgaggtatt ctaggcactc tttttagagt gccattcctg tcagt  55

<210> SEQ ID NO 12
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 12
gtgctgagtc acgaggtatt ctaggcactc tttttagagt gccattccta gtcagt    56

<210> SEQ ID NO 13
<211> LENGTH: 57
<212> TYPE: DNA
<213> ORGANISM: Artificial Sequence
<220> FEATURE:
<223> OTHER INFORMATION: The sequence is synthesized.

<400> SEQUENCE: 13
gtgctgagtc acgaggtatt ctaggcactc tttttagagt gccattccta tgtcagt    57

<210> SEQ ID NO 14
<211> LENGTH: 61
<212> TYPE: DNA
<213> ORGANISM: Artificial Sequence
<220> FEATURE:
<223> OTHER INFORMATION: The sequence is synthesized.

<400> SEQUENCE: 14
ggacctacta ctattcgtta ttgactgact tgtacttcca gaattaatcg agattgactg    60
a    61

<210> SEQ ID NO 15
<211> LENGTH: 61
<212> TYPE: DNA
<213> ORGANISM: Artificial Sequence
<220> FEATURE:
<223> OTHER INFORMATION: The sequence is synthesized.

<400> SEQUENCE: 15
ggacctacta ctattcgttt acgactgcat tgtacttcca gaattaatcg agattgactg    60
a    61

<210> SEQ ID NO 16
<211> LENGTH: 49
<212> TYPE: DNA
<213> ORGANISM: Artificial Sequence
<220> FEATURE:
<223> OTHER INFORMATION: The sequence is synthesized.

<400> SEQUENCE: 16
ctagaatacc tcgtggtgct gagtcacgag gtattctaga gtcagttag    49

<210> SEQ ID NO 17
<211> LENGTH: 53
<212> TYPE: DNA
<213> ORGANISM: Artificial Sequence
<220> FEATURE:
<223> OTHER INFORMATION: The sequence is synthesized.

<400> SEQUENCE: 17
gtgctgagtc acgaggtatt ctaggcactc tttttagagt gccattcgtc agt    53

<210> SEQ ID NO 18
<211> LENGTH: 54
<212> TYPE: DNA
<213> ORGANISM: Artificial Sequence
<220> FEATURE:
<223> OTHER INFORMATION: The sequence is synthesized.

<400> SEQUENCE: 18

```
gtgctgagtc acgaggtatt ctaggcactc tttttagagt gccattccgt cagt         54
```

<210> SEQ ID NO 19
<211> LENGTH: 55
<212> TYPE: DNA
<213> ORGANISM: Artificial Sequence
<220> FEATURE:
<223> OTHER INFORMATION: The sequence is synthesized.

<400> SEQUENCE: 19

```
gtgctgagtc acgaggtatt ctaggcactc tttttagagt gccattcctg tcagt        55
```

<210> SEQ ID NO 20
<211> LENGTH: 57
<212> TYPE: DNA
<213> ORGANISM: Artificial Sequence
<220> FEATURE:
<223> OTHER INFORMATION: The sequence is synthesized.

<400> SEQUENCE: 20

```
gtgctgagtc acgaggtatt ctaggcactc tttttagagt gccattccta tgtcagt     57
```

<210> SEQ ID NO 21
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 21

```
gtgctgagtc acgaggtatt ctaggcactc tttttagagt gccattccta gtcagt      56
```

<210> SEQ ID NO 22
<211> LENGTH: 55
<212> TYPE: DNA
<213> ORGANISM: Artificial Sequence
<220> FEATURE:
<223> OTHER INFORMATION: The sequence is synthesized.

<400> SEQUENCE: 22

```
gtgctgagtc acgaggtatt ctaggcactc tttttagagt gccattccag tcagt        55
```

<210> SEQ ID NO 23
<211> LENGTH: 56
<212> TYPE: DNA
<213> ORGANISM: Artificial Sequence
<220> FEATURE:
<223> OTHER INFORMATION: The sequence is synthesized.

<400> SEQUENCE: 23

```
gtgctgagtc acgaggtatt ctaggcactc tttttagagt gccattccag tcagtt       56
```

<210> SEQ ID NO 24
<211> LENGTH: 57
<212> TYPE: DNA
<213> ORGANISM: Artificial Sequence
<220> FEATURE:
<223> OTHER INFORMATION: The sequence is synthesized.

<400> SEQUENCE: 24

```
gtgctgagtc acgaggtatt ctaggcactc tttttagagt gccattccag tcagtta     57
```

<210> SEQ ID NO 25
<211> LENGTH: 58
<212> TYPE: DNA
<213> ORGANISM: Artificial Sequence

```
<220> FEATURE:
<223> OTHER INFORMATION: The sequence is synthesized.

<400> SEQUENCE: 25
gtgctgagtc acgaggtatt ctaggcactc tttttagagt gccattccag tcagttag      58

<210> SEQ ID NO 26
<211> LENGTH: 60
<212> TYPE: DNA
<213> ORGANISM: Artificial Sequence
<220> FEATURE:
<223> OTHER INFORMATION: The sequence is synthesized.

<400> SEQUENCE: 26
gtgctgagtc acgaggtatt ctaggcacgc ttttttagc gtgccattcc agtcagttag      60
```

OLIGONUCLEOTIDE PRIMER WITH OMEGA STRUCTURE FOR DETECTING SHORT-CHAIN RNAS AND USE THEREOF

CROSS REFERENCE OF RELATED APPLICATION

This is a national phase national application of an international patent application number PCT/CN2013/070525 with a filing date of Jan. 16, 2013, which claimed priority of Chinese application number 201210016587.6, filing date Jan. 19, 2012 and Chinese application number 201210108312.5, filing date Apr. 13, 2012. The contents of these specifications, including any intervening amendments thereto, are incorporated herein by reference.

BACKGROUND OF THE PRESENT INVENTION

1. Field of Invention

The present invention relates to a primer, and more particularly to a primer for detecting short-chained RNAs and its application thereof.

2. Description of Related Arts

Short-chain RNA plays important role in gene regulation in many biological, physiological and pathological processes. MicroRNA (miRNA) belongs to the class of RNA with the greatest number amongst short-chain RNA. Because the RNA of miRNA and its analogs DNA is very short, its discovery is relatively difficult and its existence is only discovered in recent years. In 1993, lin-4 is the first short-chain RNA with 22 nt being identified and is regulated through lin-4 messenger RNA (mRNA) of target gene, which has inhibition effect on starting of development and cell division in *C. elegan* in studies. Until 7 years later, more discoveries of short-chain RNAs with similar structure and functions in human cells are found, and it is determined that lin-4 is not an isolated member and is classified as a type of gene regulator, which is a member of microRNA (miRNA).

Afterwards, miRNA is discovered to have functional activities on different areas such as embryogenesis, development, angiogenesis, cell growth and apoptosis. It also plays a role in the course of a series of diseases such as cancer, immunodeficiency and viral infection. Lu et al. discovered that when compared to normal tissue, the miRNA expression in tumor cell always exhibits a low level. Then, miRNA expression profiles can determine low differentiation of tumor classification while the messenger RNA expression profiles from the same testing sample fails to provide an accurate result. Recently, Rosetta Genomics Ltd. have placed a series of miRNA cancer diagnostic kits into the market and claim that these diagnostic kits can accurately detect the origin of metastatic cancer cell.

Although the functions and activities of miRNA requires further research studies, more and more researches are focused on testing and application of these small molecules due to academic and medical diagnosis reasons. Recently, it is discovered that miRNA in body fluid is far more stable than its messenger RNA counterpart because of its short molecular chain and argonaute complex protection. There are many reports about the possibility of using serum or plasma miRNA expression profiles as diagnostic tools for cancer prognosis, cancer cell identification and classification.

Because the sequence is short, the nucleotide variation is small and the lack of internal control reference, the most common messenger RNA (mRNA) detection method is not suitable for the detection of miRNA with 22 nucleotides. For examples, even though the method of quantitative reverse transcriptase PCR (qRT-PCR) is the golden standard for testing in messenger RNA (mRNA) expression and expression profiles, identification methods for miRNA mostly employ short-chain RNA clone screening and expression profiles includes deep sequencing, liquid or solid phase hybridization or RT-PCR based microarrays. From the technical view point, miRNA RT-PCR has already become the most accurate and sensitive method in relation to miRNA expression profiles and identification. Accordingly, RT-PCR single-plex assay is used to verify the accuracy of the data from microarrays.

Reverse transcript refers to the cDNA synthesis reaction with RNA template under the catalysis of reverse transcriptase. Annealing and complementary of oligonucleotides to RNA chain as the starting point, then the 5' terminal to 3' terminal of cDNA, based on the complementary principles with template RNA bases, goes through the synthesis process sequentially. Through the base complementary process in the matching region, the primer and the RNA template can form a double-stranded complex, which is the necessary requirement for the start (trigger) of reverse transcript reaction. In general, in order to provide sufficient Tm and specificity so as to ensure a double-strand complex specifically formed between primer and target (not other RNA) RNA template in a tightly and stably manner, the primer usually has a length of 20-30 nt. Short-chain RNA, in particular miRNA, is a type of oligonucleotides which has a length of 18-30 nt in average. Because its length is too short, conventional primers cannot be used to trigger the formation of cDNA. In order to improve the Tm of short-chain oligonucleotide of this type, a few types of modifications can be employed. For examples, LNA oligonucleotides can be used to connect a longer and universal oligonucleotides connector to the target RNA, polyA polymerase is used to increase the length of miRNA, and primer with stem-loop structure can be used.

At present, a few and completely different types of primers and qRT-PCR kits for miRNA detection are existed in the market. The most highly recognized product is the miRNA expression profiling and detection kit from Applied Biosystems Corporation, that this product features the use of a unique stem-loop RT design. Dr Chen in Applied Biosystems established a stem-loop primer which includes an ABI unique stem-loop structure which improves short-chain RNA detection in which the base stacking effect of stem-loop primer increases the thermodynamic stability of the fully binding pairs of target RNA and probe, then increases the efficiency of RT reaction. The detection sensibility is greater than that of the linear primer by 100 times.

According to the preferred embodiment of the present invention, the "stem-loop primer" of the present invention refers to the primer with the above unique stem-loop structure. Although it is unclear how the stem-loop primers improve the specificity and efficiency of reverse transcription, its inventor claimed that primers with stem-loop structure can increase the value of hybridization temperature (Tm) of short probe through the nucleotide bases stacking effect, and can selectively promote reverse transcription of short-chain RNA. It is worth mentioning that according to the experiments of the present invention, when the template is a synthetic RNA with no internal initiation sites, the initiation effect of the linear primer is at least as well as that of a stem-loop primer. Also, no additional experiments support this theory that this stem-loop structure will increase the accuracy of RT reaction. Therefore, it is hard to understand how this nucleotide bases stacking effect can increase the efficiency of reverse transcription. It is possible that the stem-loop primer has inhibition effect on the hybridization of target sequence (internal trigger), which forms part of the reason that this kind of primer can increase the detection of short-chain RNA efficiency.

Ribonucleic acid (RNA) can serve as a template for reverse transcription to synthesize single-stranded cDNA by following Watson-Crick base-pairing rule. This type of reverse transcription requires a small fragment of oligonucleotide (the primer) to bind to the complementary binding point of the template to form a stable duplex serving as the starting point of synthesis. Once the duplex is formed, even very short-chain oligonucleotide with only a few number of nucleotide bases is sufficient for effective initiation of DNA polymerization. In a certain type of reaction system, the initiation efficiency of a RT reaction depends on the stability of the primer-RNA duplex while temperature has a great impact on the stability of the duplex. The melting temperature (Tm) of a primer-RNA duplex refers to the temperature at which half of the primer-RNA duplex is dissociated. The primer Tm depends on the primer length and the composition of the primer-RNA duplex. When binding to a complementary target, a fragment of oligonucleotide with a length of 20-30 nt is sufficient to provide the required thermostability for the primer-RNA duplex which is required for starting the RT reaction. A lower temperature is required for shorter oligonucleotide primer in order to fulfil the stability of the duplex. Under the condition of a lower temperature, the enzymatic activity is relatively lower and the efficiency of DNA polymerization reaction is very low, while the number of potential target sites is increased and the specificity of DNA polymerization reaction is very low. Meanwhile, when under the condition of a lower temperature, polynucleotide will fold to form a very strong secondary structure, causing the product of RT to become shorter when compared to the product under the condition of a higher temperature. The length of oligonucleotide does not have significant effect on RT initiation efficiency and almost all of the commercial products of RT kit select random hexamer as the primer for synthesis of the first DNA strand. When using this type of short oligonucleotide primer, internal initiation is the biggest problem while the secondary structure of short-chain polynucleotide template will not become the major problem.

The critical factors in effective primer design for multi-target short-chain RNA is to provide solutions to avoid internal initiation and formation of primer dimer while increasing the initiation accuracy at the terminal location. The oligonucleotide primer with a length of 20-30 nt can initiate the synthesis of specific fragments, while starting PCR or RT at 37° C. or above can provide sufficient complexity and thermostability. However, since the length of this type of oligonucleotide is too long, it is not suitable for use in short-chain RNA reverse transcription with microRNA (miRNA) serving as template. In view of the identification and analysis of miRNA, the difficulty lies on the big challenge on thermodynamics in relation to the length of the miRNA. A relatively short oligonucleotide can serve as a primer under a relatively low temperature condition and no adverse effect will be produced on the initiation efficiency. However, if the length is extremely short, then the loss of complexity cannot be avoided. The loss of a high level of this type of complexity will increase the number of recognition sites (internal initiation sites) within the template nucleotide and cause the problem of non-specific amplification. As the number of internal initiation sites increases, the resources for reaction is consumed competitively, causing the overall RT efficiency and level of specificity to decreased dramatically. In short, because of internal initiation, short-chain linear primer cannot be used. The complicated miRNA biogenesis relates to pri-microRNA, pre-microRNA and matured microRNA, which further complicates its detection. In addition to internal initiation, the ability of the primer to distinguish mismatches in the primer-template at the 3' terminal is another important factor affecting the RT efficiency.

As mentioned above, each of the above conventional technologies has its own limitations and restricts its applications' development. For example, LNA modification increases the Tm of oligonucleotide but adversely affects the enzymatic activities. Linear primer which has low specificity and internal initiation effect in the template nucleotide (which is not initiated from template's 3' terminal) is not qualified to be used as primer for short-chain RNA detection. Stem-loop primer, which shows a preference to binding at the 3' terminal of target RNA due to the existence of the stem-loop structure, does not have any advantages over other linear primers at least in view of the initiation efficiency.

According to the release of miRNABase v18, we learn that over 1500 different miRNAs are existed in human alone. The miRNA expressing profiling becomes more and more complicated. If no substantive changes in actual application is introduced, the use of stem-loop structure based primer for multi-target detection will become more and more difficult to operate and implement. Expression profiling based on oligonucleotide hybridization trades off sensitivity and preciseness. The result from expression profiling has to be further verified by RT-PCR. RT-PCR provides a quantitative and sensitive method for a few number of miRNA, but fails to process the increasing number of miRNA expression profiles. Now, in view of the surge of miRNA researches, a new technology for an accurate and high throughput method for miRNA expression profiling and analysis is urgently needed.

SUMMARY OF THE PRESENT INVENTION

An object of the present invention is to provide a primer for precise and multi-target detection of short-chain RNA.

In order to achieve the above object, the technical solutions according to the preferred embodiment of the present invention are as follows: an oligonucleotide primer with omega structure for short-chain RNAs detection, the primer has a 5' terminal through a 3' terminal sequentially comprising: a PCR primer target region, a variable coding region, an omega stem-loop, a spacer region for probe and a probe region, wherein a length of the PCR primer target region is 20-30 bases, a length of the variable coding region is 0-50 bases, a stem length of the omega stem-loop is 4-12 bases in pair and the bases in pair and has a cis-structure, a loop length of the omega stem-loop is 3-20 bases in non-pair alignment, a length of the spacer region for probe is at least 1 base, and a length of the probe region is 4-11 bases.

Wherein based on experimental and theoretical analyses, the PCR primer target region is selected to have 20-30 nucleotide bases because the primer with 20-30 nt can fulfil the thermostability required for a PCR and provide a sufficient complexity level of nucleotide base for identification and amplification of specific target molecules; meanwhile, the loop length of the omega stem-loop is selected to have 3-20 nucleotide bases because the number 3 is the minimum number for forming the required loop, 6-7 is the most ideal number for the loop, and negative effect on the loop formation if the number is greater than 20.

Wherein a preferred embodiment of the primer is illustrated in FIG. 1 of the drawings, wherein the nucleotide base composition comprises the sequence listing of SEQ. NO: 1, from the 5' terminal to the 3' terminal, SEQ. ID NO: 1 GTGCTGAGTCACGAGGTATTCTAG- GCTCTTTTTAGAGCCATCCTGTCAGT. The 5' end of the primer is a positive-sense primer region reserved for PCR amplification, which is PCR primer target region; the region which is upstream and adjacent to the 5' terminal of the omega stem-loop structure refers to the variable coding region, that the number and type of nucleotides in this region can be freely adjusted as long as the stem-loop structure is not affected, that the variable coding region is arranged for control a length and composition of the final product, providing the final product a corresponding label (or naming as a code) serving as the primer label for detection of different target; the omega primer with stem-loop structure ensures that the variable coding region can be freely adjusted while no structural and functional effect in relation to the primer initiation is produced. Linear primer or primer of other designs with different primer length or composition can be added but the negative effect on enzymatic reaction efficiency or the overall structural changes caused by the addition of nucleotide cannot be avoided. According to the preferred embodiment of the present invention, a secure omega stem-loop is employed to divide the structure of the oligonucleotide primer into two portions—the probe portion and the coding portion. The division at structural level allow the addition of nucleotide into the coding region while avoiding any potential effect on the overall structure or the hybridization ability in the probe region. The additional structural tension from the added nucleotide in the coding region is buffered and absorbed by the stem of the stem-loop structure and no changes or adjustment has to be made for the probe spacing or probe composition. This type of length-coded RT-PCR product can be further analysis through fluorescence spectroscopy and the resolution can reach 1 nucleotide.

The stem of the omega stem-loop has a stem structure with 4-12 pairs of pairing nucleotide bases, which is formed through the steps of: arranging a small continuous fragment of oligonucleotides in this region, and defining an adjacent fragment region belonging to the same strand of oligonucleotide which is adjacent to the small continuous fragment; and annealing with the adjacent fragment region to form a localized duplex (which is the stem) through pairing according to the rules of Watson-Crick base pairing, and has the stem structure has the function of allowing the primer-RNA duplex to form at the 3' terminal of target RNA and preventing the primer-RNA duplex from forming at complementary point in the target RNA strand;

The spacer region is a small fragment of oligonucleotide between the omega stem-loop and the probe region, which is essential for the initiation function of the omega primer of the present invention. It is necessary to arrange at least one nucleotide base as the spacer region for releasing the enzymatic activity. The optimal length for the space region is dependent on the length, the shape and the size of the stem of the omega stem-loop; the probe region is formed by a small fragment of oligonucleotide sequence, and its sequence design is in complementary pairing to the sequence of the 3' terminal of the target RNA based on the rules of Watson-Crick base pairing; the length of the probe will affect the sensitivity and internal initiation effect, and the probe with a longer length will have a higher level of RT sensitivity.

In order to form a more stable and secure structure, the stem sequence and length can be changed to obtain the same or better effect. As shown in Table 1, in general, as the number of nucleotide base pair in stem length increases, the stability of the primer structure is increased and the blocking space being provided is greater. However, through the changes in composition of the nucleotide bases, the relationship between stem length and thermostability can be adjusted. For example, changes in the composition of the deoxyribonucleotide base with a length of 12 pairing complementary bases result in similar thermostability to the ribonucleotide base with a length of 9 pairing complementary bases. This example is shown in Table 1.

TABLE 1

| Ω Stem Sequence | Stem Length | ΔG (kCal) as RNA | ΔG (kCal) as DNA | Changes in Nt | Increase in Stability as RNA (%) | Increase in Stability as DNA (%) |
|---|---|---|---|---|---|---|
| GGCTTTTTAGCC | 4 | -4.00 | -2.66 | -2 | 47.06 | 50.76 |
| GGCTTTTTTAAGCC | 5 | -4.90 | -3.66 | -1 | 57.65 | 69.85 |
| GGCTCTTTTTAGAGCC | 6 | -8.50 | -5.24 | 0 | 100.00 | 100.00 |
| GGCATCTTTTTAGATGCC | 7 | -9.60 | -6.29 | +1 | 112.94 | 120.04 |
| GGCACTCTTTTTAGAGTGCC | 8 | -12.80 | -8.13 | +2 | 150.59 | 155.15 |
| GGCACTGCTTTTTAGCAGTGCC | 9 | -15.90 | -10.52 | +3 | 187.06 | 200.76 |
| GGCACATGCTTTTTAGCATGTGCC | 10 | -17.00 | -11.57 | +4 | 200.00 | 220.80 |
| attaCACATGaTTTTTAtCATGTGtaat | 12 | -13.30 | -10.00 | +6 | 156.7 | 190.83 |
| GtcCTCTTTTGAGgaC | 6 | -8.80 | -5.06 | (0) | 103.53 | 96.56 |

In addition, it is proved that modification on the main backbone can increase stability. An example is that nucleotide bases at different locations in the omega stem is substituted by locked nucleic acid such that the use of a fewer number of complementary nucleotide bases can increase the strength of the structure. This change is sufficient to change the initiation inhibition feature within the chain or at the chain terminal. In this aspect, ribonucleotides can be used to replace deoxyribonucleotides in the stem portion to obtain identical or better effect.

The probe sequence is reversely complement to the 3' terminal of the target directly and is arbitrary in nature. The composition of the probe sequence is complement to a specific target. There are other modifications of the probe to achieve the expected result. In order to increase or decrease initiation efficiency and primer dimerization, the nucleotide of the probe can be substituted by modified nucleotide, such as locked nucleic acid (LNA) or RNA. This kind of modifications can be flexibly employed by the person skilled in the art to increase the overall efficiency of reverse transcription, to increase specificity, to inhibit dimerization or other unwanted signals caused by primer probe sequence.

Preferably, RNA with 6 pairs of pairing ribonucleotide base or DNA with 9 pairs of pairing deoxyribonucleotide base is the structure which is the most economical choice.

A second object of the present invention is to provide an application of the above primer.

The technical solution is as follows: mixing at least two primers to form a primer mixture, wherein the nucleotide base sequences of the primers in the primer mixture are different from each other.

Preferably, the application includes preparing a kit by the above-mentioned primer.

The present invention further includes any kit (or set of kit) which includes the omega primer of the present invention. The omega primer disclosed by the present invention can be prepared into an individual product for sale or as a component part in a kit for specific application.

According to another aspect of the present invention, the above primer design of the present invention can be used for individual single-target reverse transcription testing, for identification and analysis of single-target short-chain RNA, wherein its application is not limited to specific technological fields such as molecular biology, medical diagnostics, disease prognosis and forensic identification.

According to another aspect of the present invention, the above primer design of the present invention can be used for multi-target reverse transcription testing, for identification and analysis of multi-target short-chain RNA, wherein its application is not limited to specific technological fields such as molecular biology, medical diagnostics, disease prognosis and forensic identification.

Preferably, the primer of the present invention is used for detection of a single short-chain RNA or for detection of multiple short-chain RNA at the same time.

The principle is illustrated in FIG. 2 of the drawings. According to the a RT-PCR process using the omega primer of the present invention, the first step is mixing the primer and the target RNAs such that hybridization of omega primer and RNA at target sites is allowed; then the primer probe region can be complementary bound to the 3' terminal of RNA and the complementary sequence region inside the RNA chain; securely forming a duplex through complementary action at the 3' terminal of RNA which serves as the initiation point for DNA reverse transcription; wherein a conversion efficiency for incompletely binding or internal complementary pairing is very low; lastly, for further detection, utilizing target-specific primer for PCR to amplify the specific cDNA being produced;

In other words, the DNA template being produced can then be used for singleplex or multiplex amplification by real-time quantitative PCR and the product of PCR can be used for detection of single or multiple short-chain RNAs through spectroscopy, agarose gel electrophoresis and polyacrylamide gel electrophoresis;

the DNA template being produced can then be used for amplification by PCR using primer with fluorescent label and the product from PCR can be used for DNA length polymorphism analysis with automated DNA analyzer to complete the detection of multiple short-chain RNAs simultaneously.

Preferably, the fluorescent dye includes but not limited to: 6-Fam, 5-Fam, Vic, Hex, Tamra, fluorescent yellow, LiZ, Ned, Pet, cyanine 3, cyanine 5, rhodamine, Texas red and etc. (6-Fam, 5-Fam, Vic, Hex, Tamra, LiZ, Ned and Pet are trade names of products of Applied Biosystems, Inc.).

Alternately, known and synthetic oligonucleotide can be added to the RNA sample and mix together as a method for setting an internal control. The trace control template can be composed of ribonucleotides or deoxyribonucleotides.

Furthermore, the short-chain RNA is microRNA and mRNA degradation fragment, or non-coding short-chain RNAs and degraded DNA fragments, and is composed of 18-26 nucleotides.

According to one preferred embodiment of the present invention, in a single channel detection setting, the target polynucleotides is a type of microRNA (miRNA), a unique omega primer is added in which the probe sequence of the omega primer is reversely complementary to the 3' terminal of the microRNA. The two sequences are approaching each other and hybridization between the probe and the 3' terminal of the microRNA occurs to form a stable duplex. Then, the reverse transcriptase uses the sequence of the microRNA as template to extend the nucleotide chain to form a DNA. This step forms a single-strand DNA (ssDNA). This single-strand DNA includes the sequence of the 5'terminal of the omega primer and reverse complementary sequence of the 3' terminal of microRNA. Further testing of this DNA can be used as the basis for illustration of the presence and quantification of microRNA in a specific sample or sample mixtures. According to another preferred embodiment of the present invention, in a multiple channel detection setting, the target polynucleotides are a group of microRNAs. A same number of omega primer is added, each of which has a sequence reversely complementary to its corresponding target microRNA. Under this setting, the omega primer is coded by length or by composition so as to provide a label for different target for the forthcoming detection.

According to the present invention, the term 'polynucleotides' refers to the possible substrates of DNA polymerases which includes, but not limited to, DNA, RNA, DNA-RNA hybrid, modified RNA and DNA, and etc. The term 'RNA' refers to ribonucleotides, but also includes other types of polyribonucleotides.

According to a preferred embodiment of the present invention, the above target polyribonucleotides is a non-coding short-chain RNA. The non-coding RNA includes small nuclear RNA (snRNA), small nucleolar RNA (snoRNA) and small non-coding RNA (ncRNA) found in eukaryotic cells.

According to a preferred embodiment of the present invention, the above target polyribonucleotides are messenger RNA (mRNA) and messenger RNA fragment. The messenger RNA is protected by the 3' terminal of poly (A) and some mRNA, such as histone messenger RNA, is protected by modified poly (U) clusters. These distinctive features can be detected by using omega primer detection method and further developed into qualitative and quantitative methods for messenger RNA in test samples.

According to the present invention, the primer structure according to the present invention is significantly different from the existing primer and the linear primer and the differences are listed as follows:

1. The omega primer of the present invention has a secure stem-loop structural feature which can inhibit the approach of enzyme and maintain its structural construction;

2. The probe spacer of the present invention is the essential element to remove the spatial obstacle of enzymatic activity for allowing the enzyme and the probe—the target duplex to approach each other;

3. The level of blocking from the omega primer is determined by the stem length and loop size of the omega primer.

4. The structure of the omega primer of the present invention affects the thermodynamic parameters of primer-template hybrid at target site;

5. The omega primer of the present invention does not have inhibition effect on enzymatic activity.

6. The omega primer of the present invention distinguishes the mismatch at the 3' terminal through a blocking mechanism to approaching enzyme instead of relying on the increase in Tm.

In particular, the difference between the primer of the present invention and the conventional linear primer is that the primer of the present invention has a characteristic stem-loop structure serving as a stabilizer to the overall structure of the primer.

Accordingly, based on the above technical solutions, the present invention provides the following advantageous effect:

Compared the primer of the present invention with conventional linear primer, the primer of the present invention can provide equal initiation efficiency from the 3' terminal of RNA while avoiding the internal initiation and primer dimerization. Therefore, compared to conventional linear primer, the primer of the present invention has a much lower quantity requirement for detection under different instrumental settings; the omega primer of the present invention can increase the reverse transcription specificity and sensitivity through prevention of internal initiation, inhibition of primer dimerization and enhancing the probe accuracy of target hybridization at the 3' terminal. In practical application, smaller quantity of primers can be used to achieve a relatively higher RT efficiency and specificity, while in the same reaction system, different primers for different targets can be added at the same time for detection of different targets because the primers have different labels for distinguishing different detection targets produced from PCR, therefore achieving a multiplexed and high throughput detection method and dramatically increasing the detection efficacy.

Figure 1:
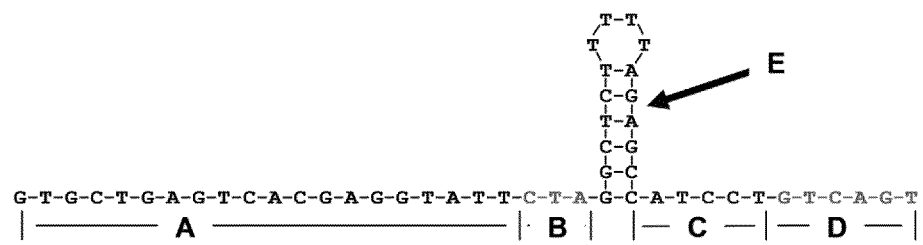
FIG. 1 is an illustration of a structure of an omega primer according to a preferred embodiment of the present invention, where A refers to PCR primer target region or PCR positive sense primer region; B refers to variable coding region; C refers to probe spacer region; D refers to probe region; and E refers to omega stem-loop.
Figure 2:
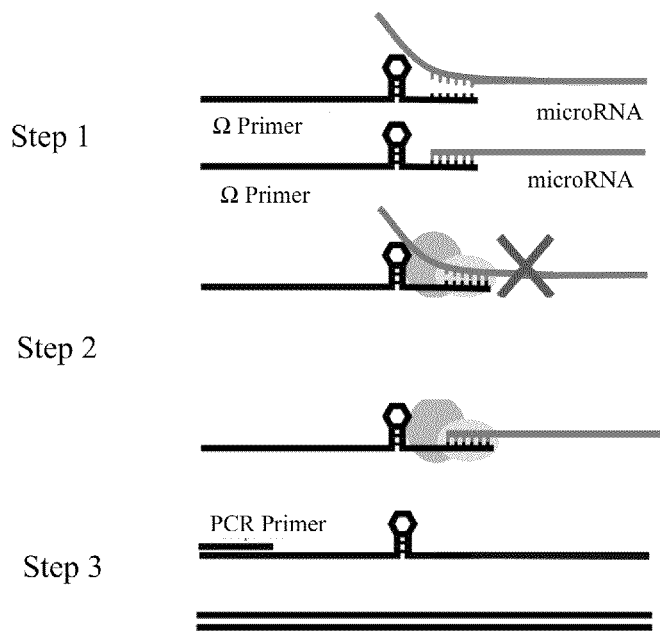
FIG. 2 an illustration of a miRNA RT-PCR amplification process with the omega primer according to the preferred embodiment of the present invention.

Table 1 refers to Distribution of Gibbs Free Energy of different stem structure. The free energy level for different stem length is calculated through mFold online computing system[10]. The stem length starts from 4-12 pair of nucleotide base which is compared in the form of RNA and DNA respectively. This shows that as the number of base pair of stem length increases, the stability of the structure of primer is increased. The 6 nucleotide base of stem-loop of Messenger RNA from human protein is used as a reference.

DETAILED DESCRIPTION OF THE PREFERRED EMBODIMENT

The present invention is further described in details with the accompanying figures and embodiments.

In order to further illustrate the object, technical feature and advantageous effect of the present invention, the present invention is further described in details with the accompanying figures and embodiments. One skilled in the art will understand that the embodiment of the present invention as shown in the drawings and described above is exemplary only and not intended to be limiting.

Embodiment 1

Figure 3:
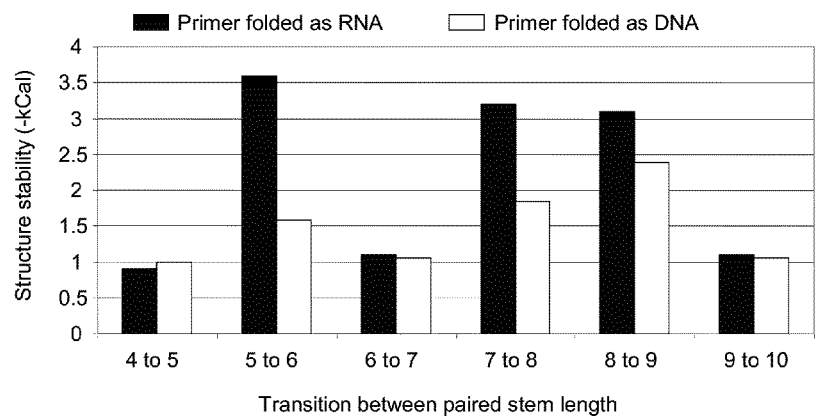
FIG. 3 illustrates a stability comparison between a RNA oligonucleotide and a DNA oligonucleotide.

Stability Comparison Experiment for RNA Oligonucleotide and DNA Oligonucleotide Referring to FIG. 3 of the drawings, RNA with 6 pairs of pairing nucleotide base or DNA with 9 pairs of pairing nucleotide base is the most economical structure. The main backbones of RNA and DNA are different, and their energy contribution for maintaining secondary structure are different. As the number of pairing nucleotides in the stem region increase, the Gibbs free energy decreases. However, the contribution to structural stability for each additional nucleotide will depend on its position. For example, in a RNA stem with 4 base pair, the addition of one nucleotide will lead to a decrease of −0.9 kcal/mole in free energy, while in a RNA stem with 5 base pair, the addition of one nucleotide will lead to a decrease of −3.6 kcal/mole in free energy. RNA with 6 pairs of pairing nucleotide base is the most economical structure, that this structure uses the least number of nucleotides to obtain the maximum free energy. RNA with 6 pairs of pairing nucleotide base is the most common form of structure, for example, this structure is used to replace the polyA tail of histone messenger RNA at 3' terminal such that the 3' to 5' terminals are protected against exonuclease degradation. The basic pairing of miRNA also only requires 6 pairing nucleotides, which is the basic number of nucleotides for a complete helix structure. For DNA, stem with 8 pairs or 9 pairs of nucleotide bases is required for providing a corresponding level of free energy of a corresponding RNA.

Embodiment 2

Function Experiment on Probe Spacing Region of Omega Primer According to the Present Invention Design and synthesize TPL6 with a fragment sequence within its chain which has the same sequence as its 3' terminal as a template.

TPL6 sequence (complementary strand): SEQ ID NO: 2

3'GTCAG TTAGA GCTAA TTAAG ACCTT CATGT TCAGT CAGTT ATTGC TTATC ATCATCCAGG5'

Omega primer with stem length of 8 base pairs is used for simulation of RT reaction, the nucleotides in italic are used to indicate the probe spacer region.

```
                                            SEQ ID NO: 3
1.  GTGCTGAGTCACGAGGTATTCTACGTGACTCAGCACGTCAGT
    stem-loop primer control SEQ ID NO: 4
2.  GTGCTGAGTCACGAGGTATTCTAGTCAGT
    linear primer control

SEQ ID NO: 5
3.  GTGCTGAGTCACGAGGTATTCTAGGCACTCTTTTTAGAGTGCC**GTC
    GT**

SEQ ID NO: 6
4.  GTGCTGAGTCACGAGGTATTCTAGGCACTCTTTTTAGAGTGCCA**GT
    CGT**

SEQ ID NO: 7
5.  GTGCTGAGTCACGAGGTATTCTAGGCACTCTTTTTAGAGTGCCAT**G
    TCGT**

SEQ ID NO: 8
6.  GTGCTGAGTCACGAGGTATTCTAGGCACTCTTTTTAGAGTGCCATC
    GTCGT

SEQ ID NO: 9
7.  GTGCTGAGTCACGAGGTATTCTAGGCACTCTTTTTAGAGTGCC
    ATTC
    GTCGT

SEQ ID NO: 10
8.  GTGCTGAGTCACGAGGTATTCTAGGCACTCTTTTTAGAGTGCC
    ATTC
    CGTCGT

SEQ ID NO: 11
9.  GTGCTGAGTCACGAGGTATTCTAGGCACTCTTTTTAGAGTGCC
    ATTCCTGTCGT

SEQ ID NO: 12
10. GTGCTGAGTCACGAGGTATTCTAGGCACTCTTTTTAGAGTGCCATT
    CCTAGTCGT

SEQ ID NO: 13
11. GTGCTGAGTCACGAGGTATTCTAGGCACTCTTTTTAGAGTGCCATT
    CCTATGTCGT
```

12. Blank control

Use 1×TE buffer solution to dissolve RT primer, concentration 50 μM. Add 1 μl primer into 500 μl $H_2O$ for dilution to form a diluted primer and each RT reaction uses 1 μl diluted primer. Use sterile water for a 10-folded dilution system of TPL6 and use dilution level $10^7$-$10^{12}$ as templates. In a 5 μl RT reaction system, 1×PCR buffer solution, 0.1×TE, 40 nM omega primer, 0.05μ/μl Taq DNA polymerase and TPL6 templates with different dilution level are used. The RT reaction requirements are: react at 37° C. for 10 minutes, 20° C. for 1 minutes and then 37° C. for 10 seconds, and repeat the above cycle for 60 times, then 37° C. for 30 minutes, 42° C. for 20 minutes and then maintain at 4° C. After the above reaction process is complete, add 25 μl of main PCR reaction solution with sense and anti-sense PCR primer into each tube. Prepare into a final volume of 30 μl by: 1×PCR buffer solution, 0.05 μ/μl Taq DNA polymerase and 50 μM primer of each type. PCR amplification requirements are: reacting at 95° C. for 4 minutes, 95° C. for 15 seconds, 61° C. for 30 seconds and then 72° C. for 20 seconds, and repeat the above cycle for 30 times, then carried out a second amplification cycle by reacting at 95° C. for 15 seconds, 61° C. for 2 minutes and then 72° C. for 1 minute, then repeat the second amplification cycle for 5 times, after that, react at 72° C. for 10 minute and then maintain at 4° C. Run the PCR product under 3% agarose gel electrophoresis, where buffer solution is 1×TB, voltage is 100V and running time is 80 minutes, then capture a photograph after running The results are shown in FIG. 4.

Omega primers with different stem lengths of 4-8 pair of nucleotide base are used in the above experiment for determining the effect of stem length and prober spacer on initiation effect. The results are summarized in FIG. 4. The synthetic TPL1 is used as Taq DNA polymerase template for simulation RT reaction. For comparing he omega primer with different stem length, use Taq DNA polymerase extension primer to complete the synthesis of DNA, then carry out PCR amplification.

Figure 4:
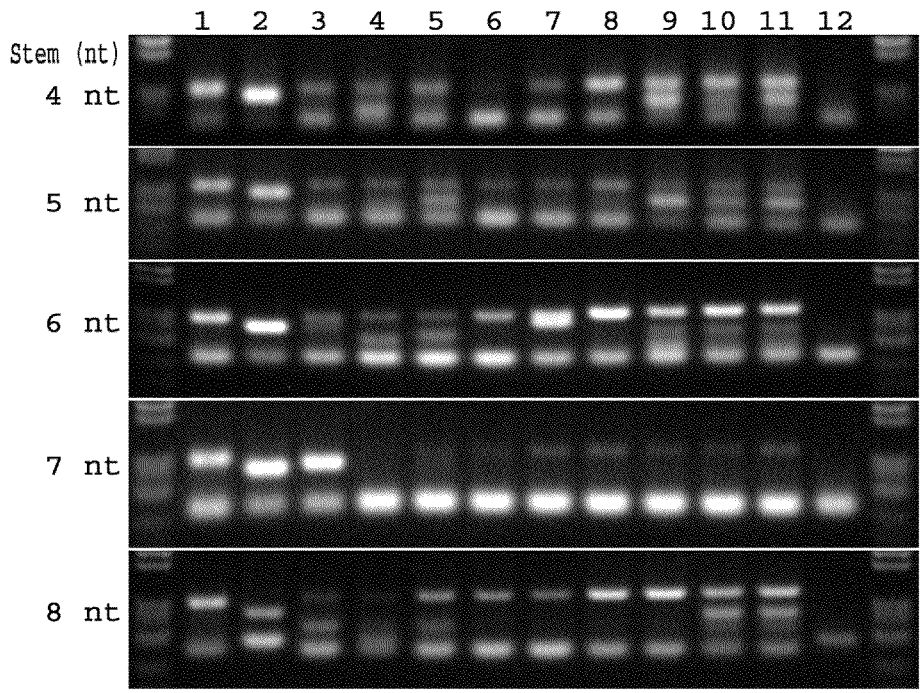
FIG. 4 shows the experimental results for illustration of the functions of the stem length and probe spacer region of the omega primer according to the preferred embodiment of the present invention; where 4 nt plate refers to the omega primer have a stem length with 4 pair of nucleotide base pair; 5 nt plate refers to the omega primer have a stem length with 5 pair of nucleotide base pair; 6 nt plate refers to the omega primer have a stem length with 6 pair of nucleotide base pair; 7 nt plate refers to the omega primer have a stem length with 7 pair of nucleotide base pair; 8 nt plate refers to the omega primer have a stem length with 8 pair of nucleotide base pair; band 1 refers to a control for stem-loop design based on reference article; band 2 refers to a linear primer; band 3 refers to an omega primer with no probe spacer region; band 4 refers to an omega primer with a probe spacer region composed of 1 nucleotide base; band 5 refers to an omega primer with a probe spacer region composed of 2 nucleotide base; band 6 refers to an omega primer with a probe spacer region composed of 3 nucleotide base; band 7 refers to an omega primer with a probe spacer region composed of 4 nucleotide base; band 8 refers to an omega primer with a probe spacer region composed of 5 nucleotide base; band 9 refers to an omega primer with a probe spacer region composed of 6 nucleotide base; band 10 refers to an omega primer with a probe spacer region composed of 7 nucleotide base; band 11 refers to an omega primer with a probe spacer region composed of 8 nucleotide base; band 12 refers to a negative control composed of sterile water.

An omega stem with 6-12 nucleotide base after modification can block the enzyme to approach to the primer-template duplex near the stem, which is shown in FIG. 4, that compared with linear primer, the DNA polymerization with omega primer has a lower reaction efficiency. By moving the complementary site through one nucleotide base for each step, the polymerase can approach the reaction site, while as the probe spacing is increased in length, the enzymatic activity is increased. As shown in FIG. 4, when internal initiation effect is neglected, and linear primer is used as control for omega primer with different stem length, the initiation of polymerization reaction is decreased dramatically, and the polymerization reaction is improved as the probe spacing is increased. This illustrates that the inhibition effect is occurred at the center region of the omega stem, and the probe spacing which provides spatial extension can offset this inhibition effect. As the stem length increases, the number of nucleotide for probe spacing to provide the offset effect on inhibition of approaching enzyme increases. For example, the enzymatic activity to stem length with 8 base pair is completely inhibited, but the addition of 5 or more nucleotide base as probe spacing can resume the enzymatic activity. This shows that the obstacle for enzyme in approaching the stem portion is affected by the distance between the probe and the stem. Accordingly, it is speculated that as more number of nucleotides is added to the probe spacing region, the behavior of the omega primer is more similar to its corresponding linear primer.

Another important factor for short-chain RNA initiation is to avoid the occurrence of internal initiation. If the probe spacing region is extended excessively, the omega primer will have all the initiation characteristic of linear primer except the inhibition effect on dimerization. However, within a narrow area, compared to the 3' terminal site, the stem structure of the omega primer shows higher level of inhibition effect to internal sites inside the chain. The inhibition area of the omega stem depends on the stem length and the loop size. In short, a longer stem length can cover a larger blocking area and provide better inhibition effect. If the probe spacing is increased, the distance between the probe and the stem is increased and the internal initiation effect inside the chain will be increased such that the omega primer behaves more similarly to a linear primer. The maximum number of nucleotide for probe spacing which can avoid the occurrence of internal initiation together with the probe length is deemed to be the effective blocking area of the omega stem structure. The blocking area is used to determine the different inhibition effect of internal initiation of different omega stems. As shown in FIG. 4, the blocking area of an omega primer with 8 base pair is 12 nucleotide, which is calculated from adding 6 nucleotide base for probe spacing and 6 nucleotide base for probe region. If 1 nucleotide base is added to the probe spacing region of this omega primer, then internal initiation is likely to occur. This result shows that the inhibition effect on internal sites within the chain and on the sites at 3' terminal are at different level. A possible explanation of this phenomenon is that the stability of probe-target duplex is affected by the position of the target site.

We believe that blocking the enzyme from approaching is the work principle of the omega primer. Also, the omega stem is also the factor for differential initiation between primer-template at 3' terminal and internal sites. The omega stem has a very significant effect on spatial configuration to its neighbor nucleotides. Since no additional nucleotide is positioned within the affected area under the spatial configuration of the omega stem, no effect on complementary process will be caused to the 3' terminal. Because the internal non-complement sites of the 3' terminal will extend into the spatial pocket of the omega stem, the forming of duplex within the RNA chain will be very difficult. This shifting of spatial configuration can thus differentiate the blocking area for the internal sites and the 3' terminal site.

Embodiment 3

Comparative Experiment on Probe Length with Respect to RT Efficiency and Effect of Internal Initiation The probe type being used are:
A: stem-loop primer+each plate illustrated below
B: Linear primer+each plate illustrated below
C: Omega primer+each plate illustrated below
Plates 1-5 uses TLP5 template with the sequence (complementary):
At 3' terminal Internal site SEQ ID NO: 14
3'-AGTCAG TTAGAGCTAA TTAAG ACCTT CATGT TCAGT CAGTT
ATTGC TTATC ATCAT CCAGG The primer probe sequence is as follows:

| Plate 1: | AGT |
| Plate 2: | AGTC |
| Plate 3: | AGTCA |
| Plate 4: | AGTCAG |
| Plate 5: | AGTCAGT |

Plate 6: Template TLP1—with no internal site, its sequence (complementary) is:

SEQ ID NO: 15
3'-AGTCAG TTAGA GCTAA TTAAG ACCTT CATGT TCAGT CAGCA
TTTGC TTATC ATCAT CCAGG

And its probe sequence is:

| Plate 6: | AGTCAGT |

Figure 5:
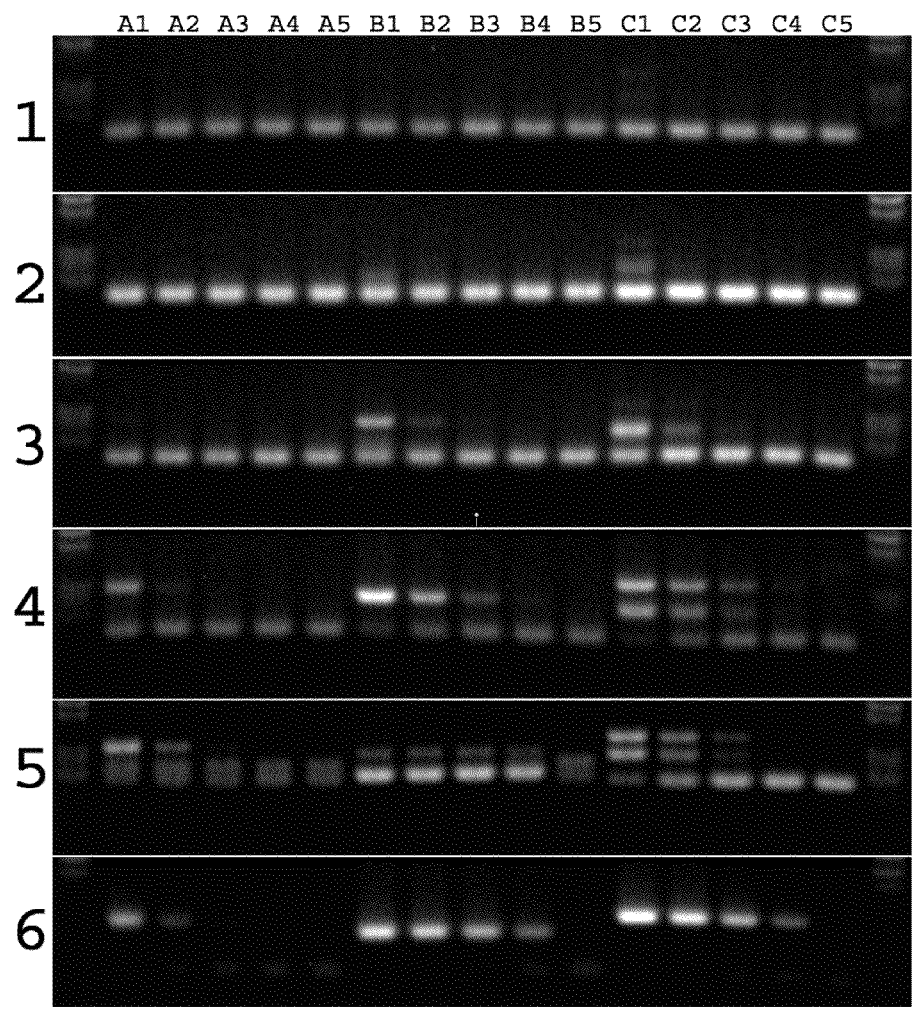
FIG. 5 illustrates the comparative effect of probe length on RT efficiency and internal initiation effect; where A refers to stem-loop primer as RT primer; B refers to linear primer as RT primer; C refers to omega primer as RT primer; wherein the template dilution is: 1: $3 \times 10^6/\mu l$; 2: $3 \times 10^5/\mu l$; 3: $1 \times 10^4/\mu l$; 4: $3 \times 10^3/\mu l$; 5: water as negative control.

Primer is dissolved in 1×TE solution, concentration 50 µM, denatured at 95° C. for 10 seconds, maintain at 65° C. for 5 min, then cooled to room temperature. Add 1 µl primer into 500 µl H$_2$O for dilution to form a diluted primer and each RT reaction uses 1 µl diluted primer. Use sterile water for a 10-folded dilution system of TPL5 and use dilution level $10^7$-$10^{12}$ as templates. In a 5 µl RT reaction system, 1×PCR buffer solution, 0.1×TE, 50 nM omega primer, 0.05 µ/µl Taq DNA polymerase and TPL5 templates with different dilution level are used. The RT reaction requirements are: react at 37° C. for 10 minutes, 20° C. for 1 minutes and then 37° C. for 10 seconds, and repeat the above cycle for 60 times, then 37° C. for 30 minutes, 42° C. for 20 minutes and then maintain at 4° C. After the above reaction process is complete, add 25 µl of main PCR reaction solution with positive-sense and negative-sense PCR primer into each tube. Prepare into a final volume of 30 μl by: 1×PCR buffer solution, 0.05 μ/μl Taq DNA polymerase and 50 μM primer of each type. PCR amplification requirements are: react at 95° C. for 4 minutes, 95° C. for 15 seconds, 61° C. for 30 seconds and then 72° C. for 20 seconds, and repeat the above cycle for 30 times, then carried out a second amplification cycle by reacting at 95° C. for 15 seconds, 61° C. for 2 minutes and then 72° C. for 1 minute, then repeat the second amplification cycle for 5 times, after that, react at 72° C. for 10 minute and then maintain at 4° C. Run the PCR product under 3% agarose gel electrophoresis, where buffer solution is 1×TB, voltage is 100V and running time is 80 minutes, then capture a photograph after running The results are shown in FIG. 5.

Probe length will affect sensitivity and internal initiation. The probe with greater probe length can achieve a better RT sensitivity. As shown in FIG. 5 of the drawings, as the probe length increases, the number of PCR product from internal initiation of RT decreases. In plate 6, when no internal site is present in the template, the efficiency is increased. On the contrary, the presence of internal site in linear primer shows a very low efficiency.

Figure 6:
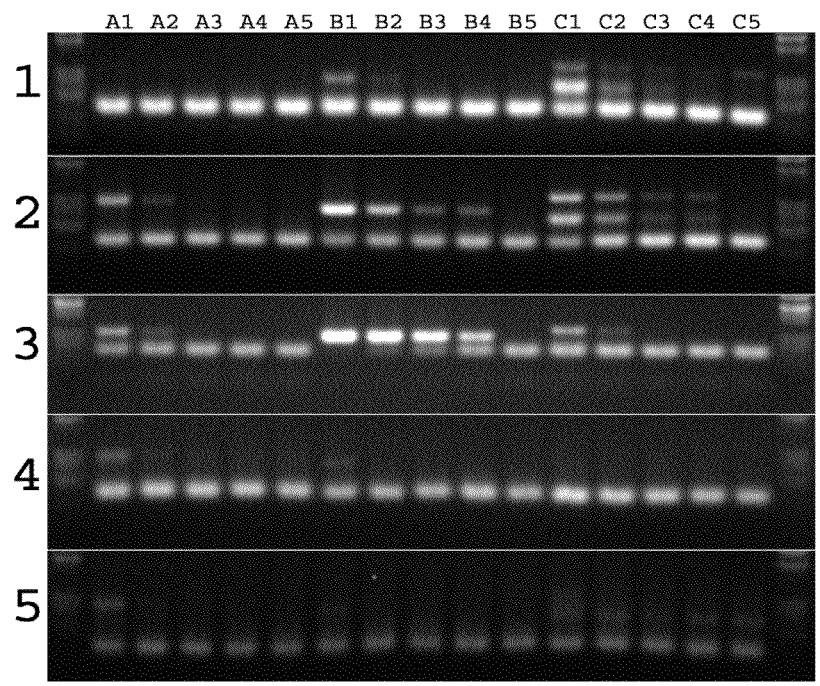
FIG. 6 illustrates the comparative results of initiation efficiency and accuracy at 3' terminal of stem-loop primer, linear primer and omega primer; where A refers to stem-loop primer as RT primer; B refers to linear primer as RT primer; C refers to omega primer as RT primer; wherein the template dilution is: 1: $3 \times 10^6/\mu l$; 2: $3 \times 10^5/\mu l$; 3: $1 \times 10^4/\mu l$; 4: $3 \times 10^3/\mu l$; 5: water as negative control.

The initiation accuracy at the 3' terminal of RNA of the primer is the critical factor affecting the overall performance of the RT primer. As shown in FIG. 6, the complement target for amplification by the omega primer shows an excellent result, compared to the mismatched primer in plate 3 or the truncated match primer in plate 1, the result is better by 100 times. In plate 3, the linear primer fails to distinguish the differences caused by a truncated match. It is not surprising that the amplification is very low for the truncated match by linear primer. In this aspect, the stem-loop primer is similar to the linear primer. This shows that the advantage of omega primer is the ability to accurately identify the correct terminal, which is the most important feature for application in multiplex detection.

Embodiment 4

Comparative Experiment for Stem-Loop Primer, Linear Primer and Omega Primer in Relation to Initiation Efficiency and Accuracy at the 3' Terminal Synthesize TPL5 with internal target ID sequence (which is bolded in the sequence listing) as template and conduct a comparative experiment for stem-loop primer, linear primer and omega primer in relation to initiation efficiency and accuracy at the 3' terminal. The TPL5 template has a specific sequence listing of 9 nt at both the 3' terminal and an internal site inside the chain, which is complement to and is identifiable by the primer probe region, the probe type is as follows:

A: stem-loop primer+each plate illustrated below
B: Linear primer+each plate illustrated below
C: Omega primer+each plate illustrated below Plates 1-5 uses TLP5 template with the sequence (complementary):
At 3' terminal   Internal site SEQ ID NO: 14
3'-AGTCAGTTAGAGCTAATTAAGACCTTCATGTTCAGTCAGTTATTG
CTTATCATCATCCAGG The primer probe sequence is as follows:

```
Plate 1:         CAGTCA
Plate 2:         AGTCAG
Plate 3:         GTCAGT
Plate 4:         TCAGTT
Plate 5:         CAGTTA
```

Primer is dissolved in 1×TE solution, concentration 50 μM, denatured at 95° C. for 10 seconds, maintain at 65° C. for 5 minutes, and then cooled to room temperature. Add 1 μl primer into 500 μl H$_2$O for dilution to form a diluted primer and each RT reaction uses 1 μl diluted primer. Use sterile water for a 10-folded dilution system of TPL5 and use dilution level $10^7$-$10^{12}$ as templates. In a 5 μl RT reaction system, 1×PCR buffer solution, 0.1×TE, 50 nM omega primer, 0.05 μ/μl Taq DNA polymerase and TPL5 templates with different dilution level are used. The RT reaction requirements are: react at 37° C. for 10 minutes, 20° C. for 1 minutes and then 37° C. for 10 seconds, and repeat the above cycle for 60 times, then 37° C. for 30 minutes, 42° C. for 20 minutes and then maintain at 4° C. After the above reaction process is complete, add 25 μl of main PCR reaction solution with sense and anti-sense PCR primer into each tube. Prepare into a final volume of 30 μl by: 1×PCR buffer solution, 0.05 μ/μl Taq DNA polymerase and 50 μM primer of each type. PCR amplification requirements are: react at 95° C. for 4 minutes, 95° C. for 15 seconds, 61° C. for 30 seconds and then 72° C. for 20 seconds, and repeat the above cycle for 30 times, then carried out a second amplification cycle by reacting at 95° C. for 15 seconds, 61° C. for 2 minutes and then 72° C. for 1 minute, then repeat the second amplification cycle for 5 times, after that, react at 72° C. for 10 minute and then maintain at 4° C. Run the PCR product under 3% agarose gel electrophoresis, where buffer solution is 1×TB, voltage is 100V and running time is 80 minutes, then capture a photograph after running.

The above experiment is carried out for probe with 3-10 nt probe length to examine the effect of stem length and probe spacing on initiation effect. The results are shown in FIG. 6. According to the results, omega prime can distinguish the correct matching or mismatching at the 3' terminal. In the plate 1, space of one nucleotide is provided between the hybridization probe and the target molecule, and the omega primer can detect molecule level in the range of $1\times10^4$; when comparing to the completely matched omega primer in the plate 2, the initiation efficiency is at least lowered by 10 times. The differential initiation of gapped base pairs by linear primer and stem-loop primer can reach 100 times. Plate 3 refers to the protruded mismatch of target molecule, the identification ability of omega primer can reach 100 times. Both linear primer and stem-loop primer cannot distinguish protruded mismatch. As the number of protruded mismatch increases, the differences of primer recognition ability will increase. Though linear primer and stem-loop primer are better than omega primer in recognizing gapped mismatches, the overall recognition ability of probe-target base pairing by omega primers is significantly higher.

Embodiment 5

Fluorescence Analysis for Omega Primer Directed RT-PCR Fragment

Figure 7:
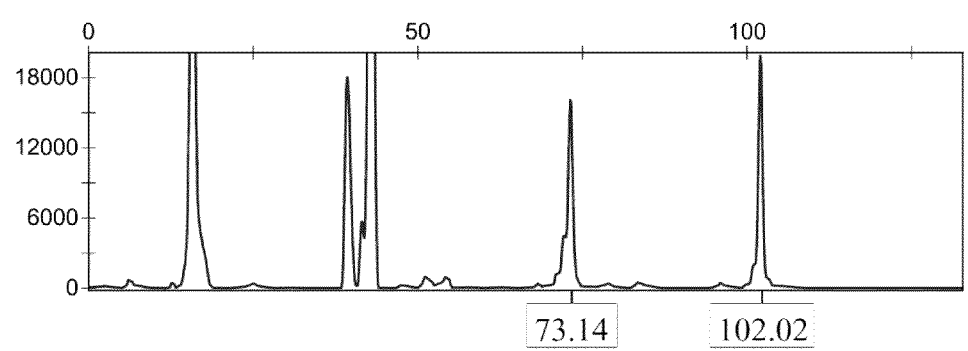
FIG. 7 illustrates the results of fluorescence analysis for omega primer directed RT-PCR fragment.

Use synthetic TPL5 with internal target ID sequence as template to compare the RT initiation effect of the 3' terminal of omega primer and internal target ID sequence. Amplified PCR products by fluorescence-labeled primers are analyzed by using ABI Prizm 310 Genetic Analyzer. The fragments resulted from internal target sites and the 3' terminal are separated by size and are analyzed quantitatively. The results are shown in FIG. 7, which illustrates that the resolution for fragment size can reach 1 nucleotide base when multiple samples are used for analysis.

Embodiment 6

Comparative Experiment on Primer Dimerization

Figure 8:
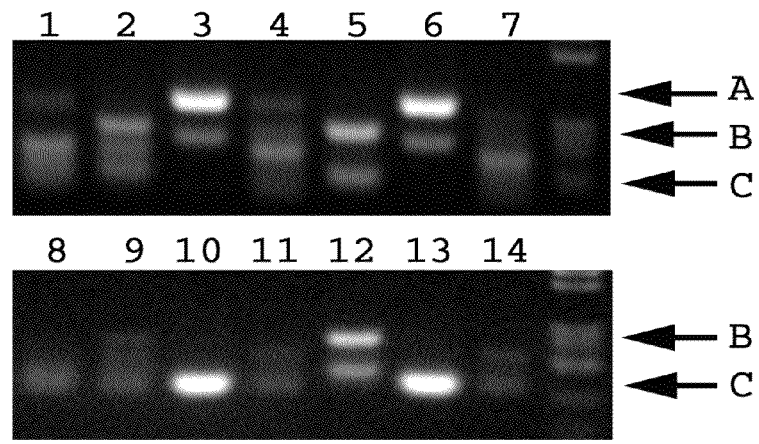
FIG. 8 illustrates the experimental results of dimerization; where band 1 refers to the stem-loop primer with 9 nt in the probe region; band 2 refers to the linear primer with 9 nt in the probe region; band 3 refers to omega primer with 9 nt and stem length of 6 pairs of nucleotides in the probe region; band 4 refers to the stem-loop primer with 10 nt in the probe region; band 5 refers to the linear primer with 10 nt in the probe region; band 6 refers to omega primer with 10 nt and stem length of 6 pairs of nucleotides in the probe region; band 7 refers to $H_2O$ control; band 8 refers to the stem-loop primer with 9 nt in the probe region; band 9 refers to the linear primer with 9 nt in the probe region; band 10 refers to omega primer with 9 nt and stem length of 8 pairs of nucleotides in the probe region; band 11 refers to the stem-loop primer with 10 nt in the probe region; band 12 refers to the linear primer with 10 nt in the probe region; band 13 refers to omega primer with 10 nt and stem length of 8 pairs of nucleotides in the probe region; band 14 refers to $H_2O$ control.

Omega primer with 6 nucleotide base stem and omega primer with 8 nucleotide base stem are compared with respect to the inhibition effect on dimerization. The primer is added into the DNA polymerase reaction system without the addition of template. The results are shown in FIG. 8 of the drawings: Arrow A is used to indicate the dimer from amplification of omega primer with 6 nucleotide base stem; band 10 and band 13 do not show the amplification band of primer dimers, that is, there is no amplification band of primer dimer in the omega primer with 8 nucleotide base stem, which illustrates that the chemical energy of the primer dimer can be inhibited by the stem-loop structure of the omega primer with 8 nucleotide base stem. Arrow B is used to indicate the dimer from amplification of linear primer, which illustrates that dimer is occurred under the same conditions in the linear primer which includes identical probe region as the omega primer; arrow C is used to indicate the monomer of omega primer after amplification; from this experiment, it is shown that the secure stem-loop structure of the present invention can prevent primer dimerization Embodiment 7

Single-Cell Analysis of RNU44 RNA from H1299 Cell Line

The testing primers are as follows:

1. LS143, stem-loop primer (control),
   SEQ ID NO: 16
   CTAGAATACCTCGTGGTGCTGAGTCACGAGGTATTCTAGAGTCAGTTAG 2. LS16, 8 base pair (bp) stem-4 nt probe spacer-6 nt probe,
   SEQ ID NO: 17
   GTGCTGAGTCACGAGGTATTCTAGGCACTCTTTTTAGAGTGCC-ATTC-GTCAGT 3. LS61, 8 bp stem-5 nt probe spacer-6 nt,
   SEQ ID NO: 18
   GTGCTGAGTCACGAGGTATTCTAGGCACTCTTTTTAGAGTGCC-ATTCC-GTCAGT 4. LS62, 8 bp stem-6 nt probe spacer-6 nt probe,
   SEQ ID NO: 19
   GTGCTGAGTCACGAGGTATTCTAGGCACTCTTTTTAGAGTGCC-ATTCCT-GTCAGT 5. LS64, 8 bp stem-8 nt probe spacer-6 nt probe,
   SEQ ID NO: 20
   GTGCTGAGTCACGAGGTATTCTAGGCACTCTTTTTAGAGTGCC-ATTCCTAT-GTCAGT 6. LS63, 8 bp stem-6 nt probe spacer-7 nt probe,
   SEQ ID NO: 21
   GTGCTGAGTCACGAGGTATTCTAGGCACTCTTTTTAGAGTGCC-ATTCCT-AGTCAGT 7. LS139, 8 bp stem-5 nt probe spacer-7 nt probe,
   SEQ ID NO: 22
   GTGCTGAGTCACGAGGTATTCTAGGCACTCTTTTTAGAGTGCC-ATTCC-AGTCAGT 8. LS140, 8 bp stem-5 nt probe spacer-8 nt probe,
   SEQ ID NO: 23
   GTGCTGAGTCACGAGGTATTCTAGGCACTCTTTTTAGAGTGCC-ATTCC-AGTCAGTT 9. LS141, 8 bp stem-5 nt probe spacer-9 nt probe,
   SEQ ID NO: 24
   GTGCTGAGTCACGAGGTATTCTAGGCACTCTTTTTAGAGTGCC-ATTCC-AGTCAGTTA 10. LS142, 8 bp stem-5 nt probe spacer-10 nt-probe,
    SEQ ID NO: 25
    GTGCTGAGTCACGAGGTATTCTAGGCACTCTTTTTAGAGTGCC-ATTCC-AGTCAGTTAG 11. LS147, 8 bp stem-5 nt probe spacer-10 nt-probe,
    SEQ ID NO: 26
    GTGCTGAGTCACGAGGTATTCTAGGCACgCTTTTTTAGcGTGCC-ATTCC-AGTCAGTTAG

12. H$_2$O

The reverse transcription initiation effect of omega primer is studied by comparing the total RNA extracted from single cell of H1299 cell line.

H1299 cell is cultured in RPMI+10% FBS culture medium. The cells is treated and collected by Trypsin-EDTA solution, and is counted in PBS solution. Then cell degradation is carried out at 37° C. in cell lysate system containing 0.4 µ/µl proteinase K and 2 µ/µl Rnase Inhibitor for 20 minutes. Protenase K was deactivated at 75° C. for 10 minutes. The total RNA equivalents of 10 cells, 1 cells, 0.1 cells, 0.01 cells, 0.001 cells are used as templates for RNU44 analysis. The above RT primer is dissolved in 1×TE solution, concentration 50 µM, denatured at 95° C. for 10 seconds, maintain at 65° C. for 5 minutes, and then cooled to room temperature. Add 1 µl of each primer into 500 µl H$_2$O for dilution to form a diluted primer and 1 µl diluted primer is used for each 10 µl RT reaction system.

The RT reaction requirements are: react at 37° C. for 10 minutes, 20° C. for 1 minutes and then 37° C. for 10 seconds, and repeat the above cycle for 60 times, then 37° C. for 30 minutes, 42° C. for 20 minutes and then maintain at 4° C. After the above reaction process is complete, add 1 µl of the RT products into 30 µl of main PCR reaction solution with sense and anti-sense PCR primer. The final concentration of Taq DNA polymerase is 0.05 µ/µl, and the concentration of each primer is 50 µM. The PCR amplification requirements are: react at 95° C. for 4 minutes, 95° C. for 15 seconds, 61° C. for 30 seconds and then 72° C. for 20 seconds, and repeat the above cycle for 30 times, then carried out a second amplification cycle by reacting at 95° C. for 15 seconds, 61° C. for 2 minutes and then 72° C. for 1 minute, then repeat the second amplification cycle for 5 times, after that, react at 72° C. for 10 minute and then maintain at 4° C. Run the PCR product under 3% agarose gel electrophoresis, where buffer solution is 1×TB, voltage is 100V and running time is 80 minutes, then capture a photograph after running.

Figure 9:
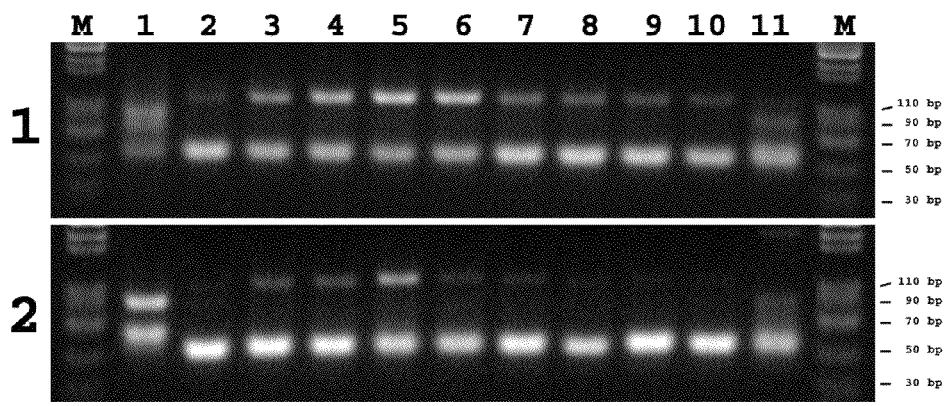
FIG. 9 illustrates the experimental results of single-cell analysis of RNU44 RNA of H1299 cell line; where plate 1: RNA which is extracted from 10 cells is added to a 10 μl RT reaction system, products from RT reaction is diluted 10 times of which 1 μl is used for amplification under 30 μl PCR reaction system; plate 2: RNA which is extracted from 1 cell is added to a 10 μl RT reaction system, products from RT reaction is diluted 10 times of which 1 μl is used for amplification under 30 μl PCR reaction system.

Each RT primer can produce a unique RNU44 band through amplification. Except the monomer primer with approximately 60 bp, the omega primer does not result in occurrence of dimerization and non-specific signal. In contrast, the stem-loop control and the water control do result in occurrence of dimerization and non-specific signal. With the use of modified RT omega primer, the RNU44 RNA in RNA from 0.5-0.00005 number of cell can be detected successfully. As shown in FIG. 9, the best resolution is obtained by omega primer with 8 bp stem, 6 nt probe spacer and 6 nt probe sequence. The amplification results of RNU44 RNA from H1299 cells are consistent with that of synthetic RNU44 template.

One skilled in the art will understand that the embodiment of the present invention as shown in the drawings and described above is exemplary only and not intended to be limiting. It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An oligonucleotide primer with omega structure for short-chain RNAs detection, characterized in that: said primer has a 5' terminal through a 3' terminal sequentially comprising: a PCR primer target region, a variable coding region, an omega stem-loop, a spacer region for probe and a probe region, wherein the length of said PCR primer target region is 20-30 bases, the length of said variable coding region is 0-50 bases, the stem length of said omega stem-loop is 4-12 bases the loop length of said omega stem-loop is 3-20 bases the length of said spacer region for probe is at least 1 base, and the length of said probe region is 4-11 bases, wherein the loop, PCR primer target region, variable coding region, spacer region and probe region are single stranded, and the stem is double-stranded.

2. The oligonucleotide primer with omega structure for short-chain RNAs detection according to claim 1, characterized in that: the stem of said omega stem-loop is a RNA with 6 pairs of bases.

3. The oligonucleotide primer with omega structure for short-chain RNAs detection according to claim 1, characterized in that: the stem of said omega stem-loop is a DNA with 9 pairs of bases.

4. The oligonucleotide primer with omega structure for short-chain RNAs detection according to claim 1, characterized in that: said bases of said omega stem-loop has a LNA modification.

5. The oligonucleotide primer with omega structure for short-chain RNAs detection according to claim 1, characterized in that: the sequence listing of said bases of said oligonucleotide primer is SEQ. ID NO: 1.

6. A kit comprising at least one oligonucleotide primer of claim 1.

7. A kit comprising at least one oligonucleotide primer of claim 2.

8. A kit comprising at least one oligonucleotide primer of claim 3.

9. A kit comprising at least one oligonucleotide primer of claim 4.

10. A kit comprising at least one oligonucleotide primer of claim 5.

11. A method of detecting one or more short-chain RNAs comprising: mixing at least two oligonucleotide primers of claim 1, wherein probe regions of said two oligonucleotide primers are different; and detecting one or more short-chain RNAs.

12. A method of detecting one or more short-chain RNAs comprising: mixing a single short-chain RNA with one or more oligonucleotide primers of claim 1 or mixing multiple short-chain RNAs with a plurality of oligonucleotide primers of claim 1; and detecting one or more short-chain RNAs.

13. A method of detecting one or more short-chain RNAs comprising: mixing one or more short-chain RNAs comprising 18-26 bases comprising microRNA, mRNA degradation fragment, non-coding short-chain RNAs or degraded DNA fragments with one or more oligonucleotide primers of claim 1; and detecting one or more short-chain RNAs.

14. A method of detecting one or more short-chain RNAs comprising: mixing at least two oligonucleotide primers of claim 2, wherein probe regions of said two oligonucleotide primers are different; and detecting one or more short-chain RNAs.

15. A method of detecting one or more short-chain RNAs comprising: mixing one or more single short-chain RNAs with an oligonucleotide primer of claim 2 or mixing multiple short-chain RNAs with a plurality of oligonucleotide primers of claim 2; and detecting one or more short-chain RNAs.

16. A method of detecting one or more short-chain RNAs comprising: mixing one or more short-chain RNAs comprising 18-26 bases comprising microRNA, mRNA degradation fragment, non-coding short-chain RNAs or degraded DNA fragments with one or more oligonucleotide primers of claim 2; and detecting one or more short-chain RNAs.

17. A method of detecting one or more short-chain RNAs comprising: mixing at least two oligonucleotide primers of claim 3, wherein probe regions of said two oligonucleotide primers are different; and detecting one or more short-chain RNAs.

18. A method of detecting one or more short-chain RNAs comprising: mixing one or more single short-chain RNAs with an oligonucleotide primer of claim 3 or mixing multiple short-chain RNAs with a plurality of oligonucleotide primers of claim 3; and detecting one or more short-chain RNAs.

19. A method of detecting one or more short-chain RNAs comprising: mixing one or more short-chain RNAs comprising 18-26 bases comprising microRNA, mRNA degradation fragment, non-coding short-chain RNAs or degraded DNA fragments with one or more oligonucleotide primers of claim 3; and detecting one or more short-chain RNAs.

20. A method of detecting one or more short-chain RNAs comprising: mixing at least two oligonucleotide primers of claim 4, wherein probe regions of said two oligonucleotide primers are different; and detecting one or more short-chain RNAs.

21. A method of detecting one or more short-chain RNAs comprising: mixing one or more single short-chain RNAs with an oligonucleotide primer of claim 4 or mixing multiple short-chain RNAs with a plurality of oligonucleotide primers of claim 4; and detecting one or more short-chain RNAs.

22. A method of detecting one or more short-chain RNAs comprising: mixing one or more short-chain RNAs comprising 18-26 bases comprising microRNA, mRNA degradation fragment, non-coding short-chain RNAs or degraded DNA fragments with one or more oligonucleotide primers of claim 4; and detecting one or more short-chain RNAs.

23. A method of detecting one or more short-chain RNAs comprising: mixing at least two oligonucleotide primers of claim 5, wherein probe regions of said two oligonucleotide primers are different; and detecting one or more short-chain RNAs.

24. A method of detecting one or more short-chain RNAs comprising: mixing one or more single short-chain RNAs with an oligonucleotide primer of claim 5 or mixing multiple short-chain RNAs with a plurality of oligonucleotide primers of claim 5; and detecting one or more short-chain RNAs.

25. A method of detecting one or more short-chain RNAs comprising: mixing one or more short-chain RNAs comprising 18-26 bases comprising microRNA, mRNA degradation fragment, non-coding short-chain RNAs or degraded DNA fragments with one or more oligonucleotide primers of claim 5; and detecting one or more short-chain RNAs.

* * * * *